United States Patent [19]
Suchsland et al.

[11] Patent Number: 5,847,207
[45] Date of Patent: Dec. 8, 1998

[54] PROCESS FOR PRODUCING 2-HYDROXY-4-METHYLTHIOBUTYRIC ACID (MHA) AND ITS USE AS FEED STUFF SUPPLEMENT

[75] Inventors: Helmut Suchsland, Rodenbach; Volker Häfner, Langenselbold, both of Germany

[73] Assignee: Degussa Aktiengesellschaft, Frankfurt, Germany

[21] Appl. No.: 793,113

[22] PCT Filed: Aug. 2, 1995

[86] PCT No.: PCT/EP95/03068

§ 371 Date: May 13, 1997

§ 102(e) Date: May 13, 1997

[87] PCT Pub. No.: WO96/05173

PCT Pub. Date: Feb. 22, 1996

[30] Foreign Application Priority Data

Aug. 12, 1994 [DE] Germany .......................... 44 28 608.2

[51] Int. Cl.$^6$ ................................................... C07C 315/00
[52] U.S. Cl. .............................................................. 562/581
[58] Field of Search ............................................. 562/581

[56] References Cited

U.S. PATENT DOCUMENTS 5,386,056   1/1995   Matsuoka ................................. 562/526

FOREIGN PATENT DOCUMENTS

| 221492 | 5/1962 | Australia . |
| 694650 | 9/1964 | Canada . |
| 0 142 488 | 5/1985 | European Pat. Off. . |
| 0 330 527 | 8/1989 | European Pat. Off. . |

*Primary Examiner*—Paul J. Killos
*Attorney, Agent, or Firm*—Pillsbury Madison and Sutro LLP

[57] ABSTRACT

Known processes for producing 2-hydroxy-4-methylthiobutyric acid (MHA) use a liquid-liquid extraction or a combined liquid/liquid and solid/liquid phase separation to isolate MHA from a reaction mixture produced by hydrolysing MMP-cyanhydrine. These processes are either costly or produce waste that is difficult to dispose of. These disadvantages are eliminated by isolating MHA by solid/liquid separation. The reaction mixture is evaporated until a MHA-containing salt residue with little or no residual water is obtained the MHA-containing, salt residue is treated with an organic solvent to produce a suspension, solid components are separated from the thus obtained suspension until a MHA-containing solution is obtained, the organic solvent is removed from the MHA-containing solution until a MHA residue is obtained and if required the MHA residue is then conditioned by water admixture. Besides high quality MHA, this process produces marketable crystalline ammonium sulphate and/or hydrogenated ammonium sulphate. This process is useful for producing feedstuff supplements.

16 Claims, 4 Drawing Sheets

PROCESS FOR PRODUCING 2-HYDROXY-4-METHYLTHIOBUTYRIC ACID (MHA) AND ITS USE AS FEED STUFF SUPPLEMENT

This application is based on German Patent Application 4428608.2 filed Aug. 12, 1994 and PCT/EP98/03068 filed Aug. 2, 1995, the contents of which are incorporated hereinto by reference.

The invention is relative to a process for producing 2-hydroxy-4-methylthiobutyric acid (MHA) according to the generic part of claim 1 as well as to the use of the MHA produced according to this process.

In particular, the invention is relative to an improved, novel process for simultaneously obtaining MHA and crystalline ammonium sulfate or ammonium bisulfate in high yield and purity while avoiding a waste water which requires treatment and optionally contains salt.

2-hydroxy-4-methylthiobutyric acid (MHA) is the hydroxy analogue of the essential amino acid methionine in racemic form and is, like the latter, an important additive in animal nutrition. In the raising of poultry MHA exhibits similar growth-stimulating properties like the amino acid known for this. However, the additive is also becoming increasingly interesting in other areas of animal nutrition.

BACKGROUND OF THE INVENTION

MHA is usually used in the form of aqueous concentrates which also contain a certain amount of oligomers, primarily the di- and trimeric linear ester acids, in addition to the monomer. The content of these oligomers is a function of the production conditions and the concentration selected. However, on account of their low nutritive efficiency and the unfavorable influence on the flow properties due to elevation of viscosity it is desirable to keep their percentage as low as possible. Commercial formulations have, at a total concentration of 8–90% by weight, less than 20% by weight, preferably less than 17% by weight in the sum of oligomers, corresponding to a monomer/oligomer ratio of ~4:1 to 5:1.

The use of the calcium salt and of the mixed calcium ammonium salt of MHA as feedstuff additive is also known. However, the production of these salts is associated with higher production costs. Moreover, they are harder to mix in as powdery solids into the feedstuff formulation than the aqueous concentrates of the free acid with a low amount of oligomers, which concentrates can be readily sprayed.

The synthesis path to MHA consists of 3 reactions.

The general process for the production of MHA starts with 3-methylthiopropionaldehyde, also designated as methylmercaptopropionaldehyde or MMP, which is reacted with hydrogen cyanide to 2-hydroxy-4-methylthiobutyronitrile, also designated as MMP-cyanohydrin or MMP-CH (equation I).

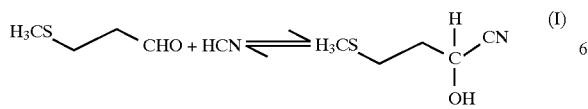

The MMP-cyanohydrin produced is subsequently customarily hydrolyzed with strong mineral acids via the intermediate stage of 2-hydroxy-4-methylthiobutyramide, also designated as MHA amide, (equation II)

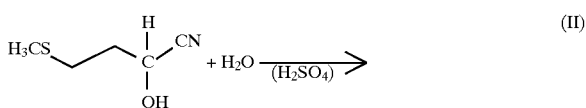

to the methionine hydroxy analog (MHA) (equation III).

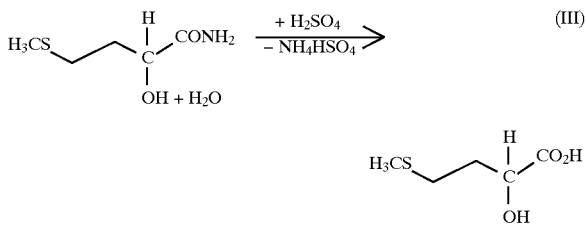

This hydrolysis can be carried out in one or in two stages.

A two-stage procedure starting with MMP-cyanohydrin is described in U.S. Pat. No. 2,745,745; 2,938,053 and 3,170,000. In them the cyanohydrin is first reacted to the MHA amide at relatively low temperatures with concentrated mineral acid, e.g. with 50–85% sulfuric acid, whereupon the hydrolysis to MHA is continued after the addition of water at elevated temperature. The calcium- or calcium ammonium salt of MHA and calcium sulfate as coupling product are obtained therefrom by treating the saponification mixture with calcium hydroxide or—carbonate. In order to reduce the compulsory accumulation of worthless byproducts the two patents cited first recommend that the hydrolysis agent sulfuric acid be added in a hypostoichiometric ratio to the MMP-cyanohydrin, e.g. 0.55–0.8:1. British patent 722,024, which describes the same type of formation of the MHA salts starting with MHA amide, implies the two-stage procedure.

The processes published in European patents 0,142,488 (with sulfuric acid) and 0,143,100 (with mineral acid), which have as subject matter the obtention of MHA in liquid form, that is, highly concentrated aqueous solutions, use the two-stage hydrolysis. The latter is obtained after the hydrolysis reaction, carried out under defined conditions of concentration and temperature via the amide stage with excess mineral acid, with the aid of a solvent extraction, in which certain solvents partially miscible with water are used. Although MHA concentrates are obtained in high quality and yield according to these processes there is the problem here of the coupling product ammonium bisulfate remaining in the aqueous raffinate. No data is presented about its use or disposal.

Concentrated MHA solutions are obtained without the aid of a solvent according to U.S. Pat. No. 3,773,927 by means of a two-stage hydrolysis of MMP-cyanohydrin with aqueous hydrochloric acid in an excess, subsequent concentration of the saponification mixture and separation of the crystallized ammonium chloride. However, the MHA concentrates obtained in this manner are rich in oligomers and colored black. Even the separated ammonium chloride is heavily contaminated.

According to U.S. Pat. No. 4,353,924 the excess mineral acid is neutralized with ammonia or other alkaline substances after the hydrochloric two-stage hydrolysis. This yields concentrated MHA solutions with lesser corrosive properties. However, the ammonium salt problem is the same. It order to eliminate this problem U.S. Pat. No. 4,310,690 describes a process in which the matter is neutralized after the hydrolysis with hydrochloric acid under precisely defined conditions with sodium hydroxide solution and the ammonium chloride converted into common salt and ammonia. In the subsequent treatment with caustic lime the MHA calcium salt is obtained as suspension in a practically saturated sodium chloride solution. After the solid-liquid separation the filtrates are returned for the most part to the preparation of the caustic-lime suspensions. In this manner the wastewater load is reduced and the co-production of ballast substances which impact the environment is avoided. No data is presented about the use or the whereabouts of the ammonia produced as secondary product.

Single-stage hydrolysis processes are also described in the patent literature. Thus, the process according to British patent 915,193 is relative to the obtention of MHA calcium salt, in which process after the saponification of MMP-cyanohydrin with dilute sulfuric acid in an excess the MHA form is separated by extraction with higher-boiling ethers from the saponification solution and MHA calcium salt obtained by subsequent treatment of the extract with calcium hydroxide. However, the return of the aqueous raffinate into the saponification stage provided in this continuous process results in an accumulation of the inorganic companions.

Another single-stage hydrolysis process with sulfuric acid as saponification agent is published in European patent 0,330,527 which makes do without solvent and results directly in concentrated aqueous MHA solutions. Crystalline ammonium sulfate in marketable form is obtained thereby as co-product. This goal is achieved in that the saponification mixture is neutralized with ammonium hydroxide solution to the extent that the excess mineral acid and the ammonium bisulfate produced are converted into the neutral sulfate, during which two liquid phases are produced which for their part are separated and concentrated by evaporation in order to obtain liquid MHA on the one hand and crystalline ammonium sulfate on the other hand. The various filtration and return steps are combined in such a manner thereby that practically no product is lost and no waste water loaded with salt is produced. The resulting MHA has a quality similar to that of the product obtained according to EP 0,142,488.

However, even this ecologically acceptable process has various disadvantages. As the applicant of the present invention determined when reworking this process, for the one, distinctly higher acid excesses than are indicated must be used, conditioned by the comparatively rather high dilution of the sulfuric acid (20–50%) in order to achieve a complete conversion of cyanohydrin. Also, in order to avoid salt separations during the neutralization the work must be carried out in a rather high dilution in order to be able to cleanly separate the two liquid phases. For the other, the isolated ammonium sulfate is of a sticky consistency and has an intensive odor, so that a posttreatment such as e.g. a wash filtration or recrystallization appears to be unavoidable, which adds additional expense to the process. Also, the process uses more energy in the evaporation steps—other than postulated—than the process of EP-A 0,142,488 cited by way of comparison. Moreover, the solid treatment provided with two separate strings with filtration/centrifugation is cost-intensive and very complex as concerns the apparatus involved as is the drying of the ammonium sulfate (not indicated in the flow chart).

In view of the state of the art indicated herein as well as of the disadvantages associated with the known processes, the invention has the problem of indicating another process for producing 2-hydroxy-4-methylthiobutyric acid (MHA) in accordance with the initially mentioned kind which should be as simple and economical as possible as regards the workup of the reaction products but at the same time largely avoids the occurrence of undesired waste substances.

SUMMARY OF THE INVENTION

These and other problems not indicated in detail are solved with a process containing the features of the characterizing part of claim 1.

As a result of the fact that during the isolation of the MHA the reaction mixture is concentrated by evaporation under obtention of an MHA-containing salt residue containing a slight residual water content to being practically free of residual water, the MHA-containing salt residue is subsequently treated with an organic solvent under obtention of a suspension, the solid components are subsequently separated from the suspension under obtention of an MHA-containing solution, the organic solvent is thereafter removed from the MHA-containing solution under obtention of an MHA residue and the MHA residue is conditioned thereafter, if necessary, by the addition of water, a process is made available in accordance with the invention which permits the production of liquid MHA with excellent quality and which in particular avoids the formation of a waste water loaded with salt and the liquid MHA accumulating along with crystalline ammonium sulfate or ammonium bi sulfate is distinguished especially by a low amount of oligomers and by a high degree of purity. In particular, the liquid MHA obtainable in accordance with the invention is essentially free of organic impurities.

Within the framework of the invention the MHA is isolated from the reaction mixture preferably by a solid/liquid separation in which an essentially solid, MHA-containing salt residue is treated with an organic, inert solvent which is completely, partially or even non-miscible with water.

This procedure clearly differs from the processes known from the state of the art in which the MHA is isolated from the reaction mixture (hydrolysate) either by liquid/liquid extraction (EP 0,142,488) or by combined liquid/liquid and solid/liquid phase separation (EP 0,330,527). Whereas the MHA isolation according to the first-named patent makes do without a solid treatment and according to the last-named patent the isolation of MHA from an MHA-containing hydrolysate proceeds without the use of a solvent, the process in the isolation of the MHA from the hydrolysate according to the present invention comprises both a solid treatment and also the use of an organic solvent for isolating the MHA but offers, in contrast to the processes known from the state of the art, the decisive advantage that it also permits, along with the production of liquid MHA with advantageous properties, especially with a low amount of oligomers, the production of one of the two ammonium salts of sulfuric acid (ammonium sulfate or ammonium hydrogen sulfate) in high purity, that is, in marketable form.

DETAILED DESCRIPTION OF THE INVENTION

A significant advantage of the novel process resides in the fact that in contrast to the process according to EP 142,488 no waste water is produced which contains inorganic salts and therefore requires treatment, the disposal and/or workup of which is problematic and cost-intensive, whereas in contrast to the process of EP 330,527 this problem is solved with lesser expenditure of energy, lesser expense for apparatuses and, as regards the obtention of ammonium sulfate or -bisulfate as co-product, with a higher product quality which makes a posttreatment not necessary. In particular, a comparison of the process of the invention with the process known from EP 330,527 shows that the energies to be expended in the last-named process for the various evaporation steps are nearly twice as high, more precisely stated, 1.8 times as high, not taking into account the energy still required for the posttreatment of the salt according to EP 330,527 for conversion into a marketable form.

The evaporation of the reaction mixture obtained after the hydrolysis in one step and the decomposition of the product mixture largely freed to completely freed of water with the aid of an inert solvent in which the MHA is soluble and the ammonium sulfate or ammonium bisulfate practically insoluble into a liquid component containing the MHA in dissolved form and into a crystalline component containing the ammonium salt which can be separated from one another are especially advantageous in the process of the invention.

The evaporation of the reaction mixture obtainable after the hydrolysis can take place in any manner known to an expert in the art.

The greatest possible freedom from water of the evaporation residue is useful in order to achieve the completest possible subsequent separation of the MHA from the MHA-containing salt residue remaining after the evaporation. On the other hand, the conditions required for evaporation are to be selected as protectively as possible so that an unnecessary damaging of the MHA-containing residue is avoided. Slight residual water contents are preferred, e.g. ≦5% (percent by weight) relative to the target product MHA. It is especially advantageous if the reaction mixture is freed essentially completely from water after the hydrolysis. The expression "freed essentially completely from water" does not denote the absolute absence of water in this connection. Rather, a residual water content which is customary under the conditions of vacuum and temperature to be preferably observed is accepted which, however, can extend to a practical freedom from residual water.

It can be especially advantageous for the invention that the evaporation of the reaction mixture is carried out in a continuous manner. A continuous process makes possible the use of very protective conditions, especially very short residence times of the reaction mixture to be freed from the water in the unit used for the evaporation. All units familiar to an expert in the art can be considered for this, including e.g. suitable evaporators such as e.g. a film evaporator equipped with rotor, and similar units.

The reaction mixture to be concentrated by evaporation and largely freed of water can be subjected, optionally and preferably before the drawing off of the water, preferably in a vacuum, before and/or during the actual evaporation to an adiabatic evaporation cooling under application of a vacuum to approximately 60° C. or less in order to remove any volatile or odor-intensive components of the reaction mixture. This has the additional effect that these components can be held separate from the main amount of the water to be drawn off later.

It is furthermore advantageous if the saponification solution, that is, the reaction mixture, is treated after treatment with sulfuric acid with ammonia, preferably gaseous, and is neutralized thereby either up to the complete formation of ammonium sulfate or only partially to the blunting of any free sulfuric acid still present. This step can also be eliminated in the case of the striven-for byproduct ammonium bisulfate.

It can also be preferred in a large-scale realization of the process of the invention that the ammonium sulfate salts obtained after the solid/liquid separation in solid form are conducted, optionally after previous evaporation of solvent remnants and being slurried with water, to a sulfuric acid—contact system under recovery of sulfuric acid.

It is furthermore also possible that the evaporation of the reaction mixture is carried out without previous or subsequent neutralization with ammonia and that the ammonium bisulfate obtained after the solid/liquid separation in solid form is conducted, optionally after previous evaporation of solvent remnants and being slurried with water, to a sulfuric acid—contact system under recovery of sulfuric acid.

There is a plurality of solvents which are possibilities for the substance separation (take-up of the bottom product largely to completely freed of water and separation of the liquid from the solid phase) and which meet the conditions of chemical indifference and low solubility for ammonium sulfate and/or ammonium bisulfate. Suitable solvents can be miscible with, partially miscible with water or even water-insoluble. The following can be taken into consideration: E.g. ethers such as isopropyl ether, tetrahydrofurane, dimethoxyethane, secondary alcohols such as 2-propanol, secondary butyl alcohol, ketones such as acetone, methylethylketone, methylisopropylketone, methylisobutylketone, aromatic hydrocarbons such as toluene, chlorinated hydrocarbons such as carbon tetrachloride and others. Primary alcohols, esters and aliphatic and cycloaliphatic hydrocarbons are less suitable. Polar solvents which have comparatively low boiling points and heat of evaporation and which can be recovered readily by distillation, optionally under rectifying or azeotrope-forming conditions, have proven to be especially suitable from an engineering standpoint. Care must moreover be taken in the case of (partial) miscibility with water that the water content should not exceed 5% by weight in a possible recycling of the solvent. Solvents preferred within the scope of the invention are acetone, methylisopropylketone, methylisobutylketone, isopropanol, tetrahydrofurane and toluene. Acetone is especially preferred. Even mixtures of the previously cited solvents can be used in accordance with the invention.

In the invention a suspension containing in particular salt precipitating in a crystalline manner (ammonium sulfate or ammonium bisulfate) develops from a gelatinous mass obtained as MHA-containing salt residue after the condensation by evaporation by the addition of a solvent in accordance with the invention. Finally, the salt precipitated in a crystalline manner and obtained by the addition of the solvent in the form of a suspension is separated under obtention of an MHA-containing solution. This separation can basically be carried out according to all process variants known to an expert in the art for the separation of solids out of solutions. Processes used with preference are filtration under the influence of gravity or also centrifugation. The ammonium salts crystallized out and separated in this manner are optionally washed with the solvent used and then dried. Ammonium sulfate or ammonium bisulfate obtainable and treated in this manner is essentially free of organic impurities and is of sales quality with a degree of purity of ≧99%.

The MHA-containing solution obtained after the separation of the solid components out of the suspension as filtrate or centrifugate (organic phase) is treated further in accordance with the invention for the isolation of the MHA contained in it. This preferably takes place by evaporating off the solvent, optionally under rectifying or azeotrope-forming conditions, during which it is furthermore preferred that the recovered solvent contains no or at the most up to 5% by weight water. It is again preferred in this connection, in order to avoid any possible damage to the MHA, to keep its thermal loading as low as possible by applying a vacuum.

The MHA obtainable after the evaporating off of the solvent out of the MHA-containing solution is already of a high quality and capable of being sold. However, water can be optionally added for conditioning to the MHA flowing off out of the evaporation of the organic phase under protective conditions in order to obtain liquid MHA in a desired concentration of approximately 85–90% by weight (including oligomers).

Furthermore, the process of the invention should be designed to be selectively continuous or intermittent as regards the carrying out of the process steps evaporation—crystallization—filtration/centrifugation—solvent recovery and final dilution of the liquid MHA. The continuous or intermittent operation makes possible an especially protective thermal product treatment with total residence times of the MHA from the end of the hydrolysis to an optional dilution with water of less than 60 minutes, preferably of less than 30 minutes. Furthermore, this type of isolation assures in an especially advantageous manner the obtention of an approximately 85–95% by weight liquid MHA product with extremely little discoloration, good flow property, good thermal stability and with comparatively low amount of oligomers of at the most 17% by weight, preferably less than 15% by weight relative to the final product.

In a further aspect the process of the invention also improves, in addition to the isolation of the MHA from the reaction mixture obtained by hydrolysis with sulfuric acid, the hydrolysis of the MMP-CH itself. Thus, in a process variant preferred in accordance with the invention the hydrolysis of the MMP cyanohydrin is carried out in two stages with the MHA amide being obtained in a first stage and the MHA in a second stage. The hydrolysis of MHA amide is preferably carried out in a first stage with 60–85%, preferably 65–75% sulfuric acid in a molar ratio of 1:0.5 to 1:1.0, preferably 1:0.55 to 1:95 at temperatures between 20° and 60° C., preferably 30°–50° C. The MHA amide is produced thereby essentially from the MMP cyanohydrin and the mixture being produced is furthermore essentially and advantageously practically free of non-converted cyanohydrin.

Furthermore, it is preferred in accordance with the invention that the hydrolysis of the MHA amide obtained in the first stage is carried out in a second stage by the addition of water and at the very least further sulfuric acid up to the stoichiometric upper limit at temperatures of 90°–110° C. preferably under reflux conditions in order to complete the hydrolysis of the MHA amide to MHA. The two-stage hydrolysis of the MMP cyanohydrin is to be carried out within the scope of the invention with sulfuric acid which is more highly concentrated in comparison to the state of the art in a hypostoichiometric to at the most stoichiometric ratio. In the case of hypostoichiometric dosing in the first hydrolysis stage (amide formation) more sulfuric acid can be supplied at a lower temperature in order to shorten the reaction time in the second stage, optionally until reaching the upper stoichiometric limit at elevated temperature in order to complete the conversion of the amide to the acid.

On the whole, the process of the invention together with the cited preferred embodiments of the process makes possible a savings of raw materials, that is, of sulfuric acid by using hypostoichiometric to at the most equal equivalents; at the same time crystalline, marketable ammonium bisulfate or ammonium sulfate can be obtained along with the liquid MHA striven for as final product without formation of a waste water loaded with salts at relatively low expenses for energy and total conversion.

BRIEF DESCRIPTION OF THE DRAWINGS

Further aspects of the present invention result from the examples described in the following in which reference is made to the attached figures.

EXAMPLES

Example 1

Production of 2-hydroxy-4-methylthiobutyronitrile (MMP-CH)

Figure 1:
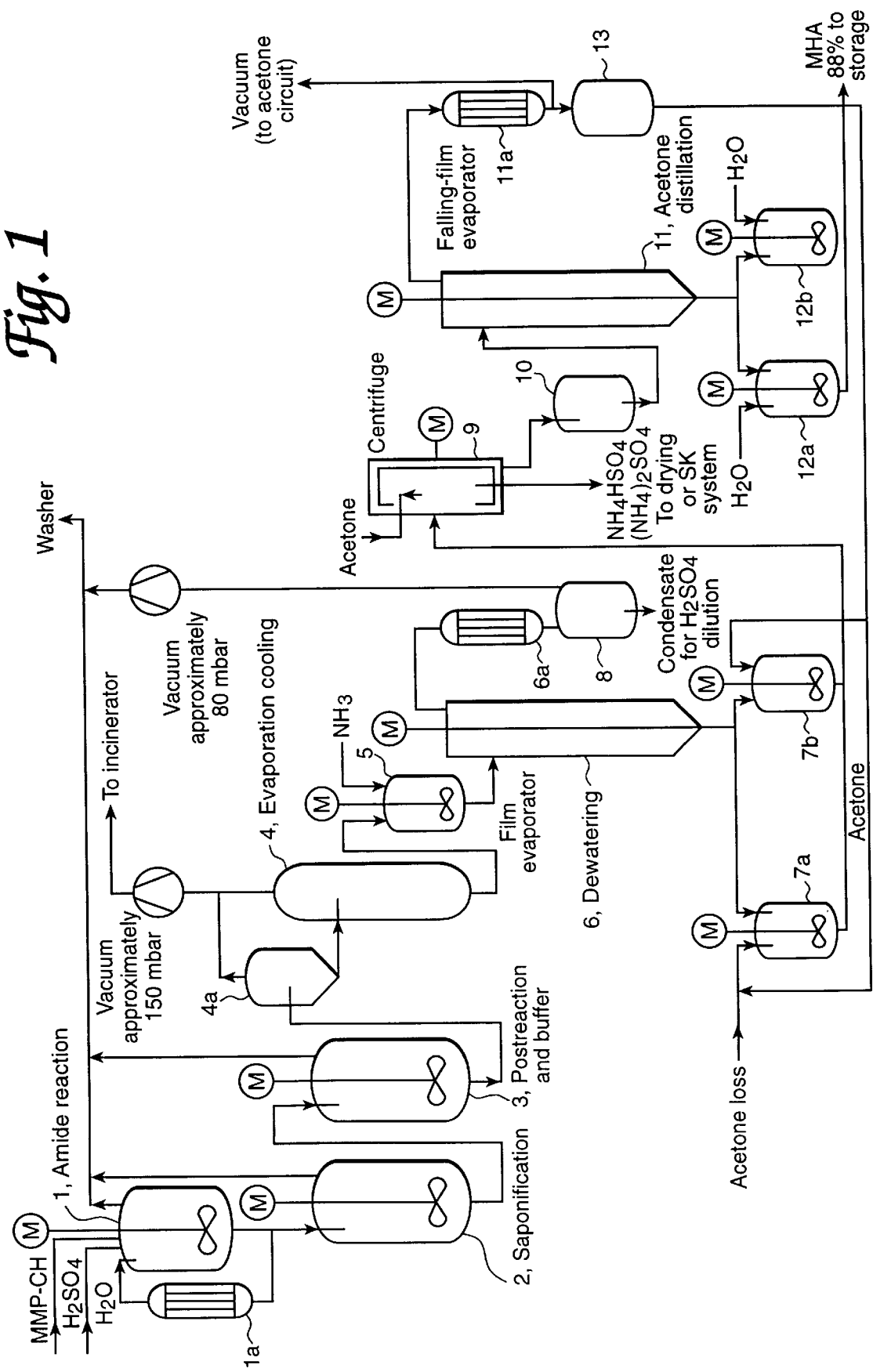
FIG. 1 shows a schematic survey for a first industrial variant of the process of the invention for producing MHA.

513.8 g 99.0% 3-methylthiopropionaldehyde (4.883 moles) were placed in a coolable reaction container provided with pH electrode. The pH was raised with triethylamine from 6.2 to 7.5. Then 135.1 g 99.0% hydrogen cyanide (4.993 moles) were introduced at 30° C.±2° C. under intensive agitation and cooling within 30–45 minutes during which the pH of the reaction solution was held constant at 7.5 by the further addition of triethylamine. At the end of the inflow of hydrogen cyanide a total of 1.08 g triethylamine had been consumed. The cooling was then removed and the solution agitated a further 30 minutes at 30° C. After having cooled down to ambient temperature 649.6 g of a 98.6% solution of 2-hydroxy-4-methylthiobutyronitrile were obtained which was stabilized by the addition of 85% phosphoric acid at a pH of 2.6. Analysis yielded a conversion yield of 99.96% relative to 3-methylthiopropionaldehyde added.

Example 2

150.2 g 65.3% sulfuric acid (1.0 mole) were placed in a reaction container equipped with intensive agitator at 50° C. Within 30 minutes 133.1 g 98.6% MMP-CH (1.0 mole) were added at this temperature under intensive agitation and cooling. The mixture was allowed to react a further 30 minutes at unchanged reaction temperature whereupon the complete conversion of the cyanohydrin to 2-hydroxy-4-methylthiobutyramide (MHA amide) was determined by HPLC analysis. The reactor contents were then diluted with 95 g water, heated to 90° C. and agitated for 150 minutes at this temperature. After the completion of the hydrolysis of the amide stage to the free acid MHA had been ascertained by HPLC analysis a vacuum was applied and the temperature of the reaction mixture lowered to approximately 70° C. under evaporation cooling. Approximately 8 g of volatile components were stripped thereby. The dealcoholized solution was treated for the conversion of the acidic ammonium sulfate formed in the reaction into neutral ammonium sulfate with 1 mole gaseous or concentratedly [sic] aqueous ammonia. Then, the water was completely evaporated off as quickly as possible in a rotating flash evaporator under a vacuum and the remaining bottom product taken up with 200 g acetone. The MHA went into solution thereby whereas the insoluble ammonium sulfate settled in crystalline form. The salt was filtered off, rewashed with 25 g acetone and dried. 130 g 99.95% ammonium sulfate were obtained. The combined acetonic filtrates were freed of solvent in a rotating flash evaporator and the resulting bottom product diluted with approximately 20 g water so that an approximately 88% MHA solution was obtained. The yield of MHA including oligomers was 98.5% relative to MMP-CH added. The product had a yellowish color. It has a content of 11.0% of dimeric and less than 2% of trimeric constituents.

Examples 3–8

The process described in example 2 was followed; however, instead of acetone the following solvents were used in succession for the salt—product separation: Isopropanol, methyl-t-butylether, tetrahydrofurane, ethyl acetate, toluene, methylethylketone and methylisobutylketone. Practically identical results for MHA and ammonium sulfate were obtained. The amount of dimers fluctuated between approximately 10 to approximately 13%, the amount of trimers was below approximately 2%. When tetrahydrofurane was used as separating agent the matter was repeatedly rewashed on account of the poorer filterability.

Example 9

1 mole 98.6% MMP-CH was converted to MHA as described in example 2 with 1 mole sulfuric acid. After the reaction was completed the hydrolysate was evaporated without preceding neutralization with ammonia under a vacuum until constancy of weight. The practically anhydrous bottom product was treated with 200 g acetone. The resulting suspension was centrifuged, the filter cake washed with 25 g acetone and dried. Filtrate mother liquor and wash solution were combined and distilled free of solvent under a vacuum. 148.7 g of an oily residue were obtained, corresponding to a total yield of 99% MHA which yielded after dilution with water an approximately 88% MHA solution colored yellow with good flow properties and good thermal resistance. The dimer content was determined at 15.1% whereas the trimer content was below 1.5%. In addition, 113 g crystalline, practically pure ammonium bisulfate were obtained in flowable form.

Example 10

80 g 98% sulfuric acid (0.8 mole) were diluted with 40 g water (65.3%) in an apparatus with intensive agitator and reflux condenser and heated to 50° C. 133.1 g 98.6% MMP-CH (1.0 mole) were allowed to flow in under thorough mixing and agitation within a period of 30 minutes. After another 30 minutes at 50° C. an HPLC analysis indicated the complete conversion of the MMP-CH to the intermediate hydrolysis product. The viscous mixture was diluted with 75 g water (40.2%) and heated to 100°–102° C. After 3.5 hours of boiling under reflux conditions the reaction was completed and no more MHA amide was able to be demonstrated. The brownish-colored solution was cooled down by evaporation cooling to 65° C. Approximately 15 g volatile constituents were removed thereby. Then 13.7 g ammonia gas (0.8 mole) were bubbled in for neutralization, whereafter the mixture was evaporated in a flash evaporator until constancy of weight. 260 g of a viscous, gel-like reaction mass remained which was taken up in 200 g acetone. The resulting suspension was filtered, the filter residue digested twice with 25 g acetone per time and dried. 106 g 99.7% pure white ammonium sulfate were obtained. The combined filtrates were evaporated to dryness on a rotary evaporator. 151 g oily MHA concentrate were obtained which was diluted with water to a content of about 88%. The dimer content in the concentrate was 13.8% and the trimer content was below 1.5%. The solution has a brown color.

Example 11

Example 10 was modified in such a fashion that 1 mole MMP-CH was brought to reaction with 0.9 mole sulfuric acid in the same concentration ratio (1st stage 65.3% aqueous, 2nd stage 40.2% aqueous) but with the further measures that the intermediate hydrolysis product was boiled 3 hours under reflux (100°–102° C.) and 0.90 mole ammonia was used for the neutralization. After the product decomposition with acetone and subsequent workup as described, 150 g MHA with a dimer content of 16.2% (99.9% total yield) were obtained which yielded a brownish-colored solution after dilution to 88%. In addition, 119 g pure white ammonium sulfate were obtained.

Example 12

Example 2 was repeated; however, the hydrolysis time in the 2nd stage was shortened to 1.75 hours whereas the reaction temperature was raised to 100°–102° C. After the product decomposition with acetone and workup 151 g MHA concentrate with 11.0% dimer content and less than 2% trimer content were obtained which yielded after dilution to 88% a brown-colored solution with satisfactory flowability and thermal stability. In addition, 129 g pure white ammonium sulfate with a content of 99.7% were isolated.

Example 13

Example 2 was repeated; however, 1.15 moles ammonia gas were used for neutralization and the time of vacuum evaporation and of acetone dealcoholization limited to 15 minutes. The yields of MHA and ammonium sulfate were quantitative. The MHA concentrate was 98.0% with a dimer content of 8.7% and still contained 2.0% ammonium sulfate. No more trimers were able to be demonstrated. The yellow-colored solution diluted to 88% active substance content displayed excellent flowability and thermal stability.

Example 14

3 moles MMP-CH corresponding to a molar ratio of 0.55:1 were added to 216 g 75% sulfuric acid in the course of 30 minutes at 50° C. After 30 minutes of reaction time the cyanohydrin was completely converted to the intermediate hydrolysis product consisting essentially of MHA amide along with little MHA. The mixture was then diluted with 240 g water to a sulfuric acid content of 35.5% without organic components and divided into 3 equal parts.

Part (1) was heated to 104° C. and agitated 4.5 h under reflux boiling, during which 35 ml water and more volatile components were distilled off after 2.5 h. After the reaction was completed the workup described in example 9 was followed.

Part (2) was compounded with 20 g 98% sulfuric acid, whereafter the molar ratio was 0.75:1 and the sulfuric acid concentration raised to 42.8%—basis organically free. The mixture was then heated to 106° C. and held 2 h under reflux. After the reaction was completed the workup described in example 9 was followed.

Part (3) was compounded with 40 g 98% sulfuric acid, whereafter the molar ratio of acid to MMP-CH and MHA amide was 0.95:1 and the sulfuric acid concentration raised to 48.5%—basis organically free. The mixture was then held under reflux at 108°–109° C. for 1 hour. The workup described in example 9 was then followed. The results can be gathered from the following table.

TABLE

| No. | Tot. yield % | MHA mon. % | Dimers % | MHA amide | Color | Ammonium salt* |
|---|---|---|---|---|---|---|
| 14-1 | 94.0 | 91.9 | 4.3 | 2.9 | dark brown | 57.6 |
| 14-2 | 96.1 | 84.7 | 14.2 | 1.1 | brown | 80.2 |
| 14-3 | 97.6 | 81.3 | 16.3 | 0.1 | yellowish brown | 107.2 |

*The isolated ammonium salt is a mixture of acidic with neutral ammonium sulfate with an amount of the former which increases in the direction 14-1 to 14-3 in correspondence with the molar ratio.

Example 15

1 mole MMP-CH was placed in a reaction container. 89 g 75% sulfuric acid (0.68 mole) was charged between 25°–30° C. in the course of 60 minutes under thorough mixing and cooling. After a further 60 minutes of agitation at 50° C. the cyanohydrin was completely converted and could no longer be demonstrated analytically. The intermediate hydrolysis product was diluted with 180 g water, heated until reflux boiling and hydrolyzed 3 hours at 108° C. The reacted solution was completely evaporated on a rotary evaporator in a vacuum and the remaining residue digested with 200 g acetone. After filtration of the suspension obtained, washing out of the filter residue with 2 times 25 g acetone, evaporation of the filtrate, 150 g MHA final product was obtained with a dimer content of 6.5% which was diluted with water to an 87% brown-colored solution. At the same time 77 g of a pure white salt mixture of ammonium bisulfate+ammonium sulfate (98.3%) was obtained after the drying.

Example 16

A hydrolysis solution was produced and dealcoholized as described in example 2. After the addition of 68 g 25% ammonia 443 g of a product mixture were obtained which had the following composition: 33.5% MHA with 7.5% dimers, 29.3% ammonium sulfate and 37.1% water. This mixture was evaporated to low bulk at 90° C. under a vacuum until a weight of approximately 300 g, whereafter the dimer content had risen only insignificantly to 7.6%. The mixture was then digested with 290 g methylisobutylketone (MIBK) and the residual water (~21 g) distilled off azeotropically at 88° C. The resulting suspension was worked up further in analogy with example 2. 148.7 g MHA with a content of 8.9% dimers and less than 1% trimers as well as 131 g pure white ammonium sulfate were obtained. After dilution of the MHA to a concentration of 88% a pale yellow solution was obtained with excellent flowability and good thermal stability.

Example 17

10 moles MMP-CH were reacted in an agitating apparatus with the same number of moles of sulfuric acid in accordance with the process described in example 2. The raw hydrolyzate was dealcoholized under removal of 80 g volatile components by vacuum evaporative cooling to approximately 65° C. and subsequently neutralized with 10 moles 25% ammonia. The resulting solution was now charged continuously into a heated Sambay evaporator standing under a vacuum to which a condensate cooler and distillate receiver were connected at the top side and two cooled receiver changers provided with agitators were connected at the runoff side. The dewatering took place at 90° C./80 mbar, during which the product charging was regulated in such a manner that the concentrate running off had only a minimal residual water content of less than 1% which was continuously regulated by means of Karl-Fischer titration. The bottom product was alternatingly let into the receiver changers loaded with aliquot amounts of acetone until the same filling height in each one and the suspensions produced still remained capable of being agitated. The individual fractions were separated after the stress relief in a laboratory skimmer centrifuge, the centrifugates subsequently washed with a little acetone and dried after the union. The centrifuge filtrates running off into a collecting tank were fed continuously into a falling-film evaporator equipped with receiver changers and condensation devices and dealcoholized free of solvent under a vacuum. The concentrate running off was alternatingly taken up into the bottom receivers loaded with proportionate amounts of water under agitation and cooling and enriched up to a content of about 88% final product. The individual fractions were united in a storage container and homogenized in conclusion. After the end of the product workup 98.8% MHA was obtained containing 11.5% dimers, 1.8% trimers and 0.4% ammonium sulfate as 88% yellow solution. The yield of crystalline ammonium sulfate was 95.5%.

The production of MHA and ammonium sulfate and bisulfate described in the present example is shown in schematic fashion in FIG. 1 as an industrial process with the main apparatuses.

The industrial device schematically shown in FIG. 1 with the main apparatuses is operated as follows in a process in accordance with the method of operation described in examples 2 and 17 with batchwise production and continuous workup of the target products:

An approximately 65% sulfuric acid is prepared and placed in a first agitator reactor 1, whereupon the conversion to MHA amide takes place by the addition of the MMP cyanohydrin in the same stoichiometric ratio or also with a slight deficit of mineral acid at approximately 50° C. while the reaction heat is removed via an external cooling circuit. After the cyanohydrin has been completely converted within a postreaction time the mixture is discharged into a second agitator reactor 2, whereupon the hydrolysis of the MHA amide to the acid MHA is essentially concluded after dilution to an approximately 40% concentration of sulfuric acid under elevation of temperature at approximately 95° C. The mixture is then transferred into a third agitator container 3 which functions both as a postreactor as well as a buffer. From there the mixture is continuously fed into a container combination standing under a vacuum and consisting of separator 4a and expansion tank 4 during which the mixture is cooled down to approximately 70° C. while at the same time volatile impurities and a proportionate amount of water are drawn off which are fed in gaseous form or condensed to an incinerator. After the stress relief the dealcoholized mixture passes into a further agitator container 5 in which a concentrate is obtained in continuous fashion by the pH-controlled addition of ammonia until the complete neutralization of the sulfate ions under formation of ammonium sulfate, which concentrate is fed into film evaporator 6 standing under a vacuum and equipped with a rotor with condensation system 6a and 8. At approximately 90° C. the concentrate is dewatered in a vacuum under flash vaporization to the extent that the bottom product discharged in the form of a gel contains only slight residual water contents of approximately ≧5% relative to MHA+oligomers. The bottom product is now let off alternatingly under stress relief in receiver changers 7a and 7b loaded with the solvent, e.g. acetone, at which time the ammonium sulfate crystallizes out while the MHA goes into solution. The ratio of product to solvent is selected so that suspensions which are still capable of being agitated are produced. In the case of acetone a ratio of 1:1.5–2.0 is sufficient. The aliquot suspension fractions are supplied intermittently to skimmer centrifuge 9 and subsequently washed both separately and with the solvent.

The resulting filter cake fractions are united and optionally supplied to an evaporating posttreatment (not sketched into the schema) for the purpose of recovering any still-adhering solvent remnants. The filtrate running off into collecting tank 10 and consisting of mother liquor and wash solution is fed continuously into a film evaporator or falling-film evaporator standing under a vacuum and provided with the appropriate peripheral equipment and completely freed of solvent at 80°–90° C. under flash vaporization— optionally under rectifying conditions in order to prevent an accumulation of water. The drawn-off solvent is supplied after liquefaction in condenser 11a to collecting tank 13 and returned after appropriate replacement of loss into the circuit process. The bottom product which is discharged under stress relief out of the evaporator and is almost to completely anhydrous is taken up alternatingly under cooling in the two agitator receivers 12a and 12b loaded with proportionate amounts of water, enriched up to a final product content of about 88–90% and then transferred to storage. The aqueous vapor condensate evaporated off in the dewatering stage, liquified in condenser 8 and caught in collecting tank 8 can be used for diluting the sulfuric acid in the first and also in the second reaction stage of the process, which reduces the waste water to insignificant residual amounts stemming from the gas washers.

Example 18

Further hydrolysis batches were produced from 10 moles MMP-CH each in accordance with the general process of example 2 and dealcoholized by evaporation cooling to 65° C. However, the obtention of the final product took place differently from the method with methylisobutylketone (MIBK) described in example 17 for product separation using the process schema illustrated in FIG. 2:

The batches neutralized in agitator container 1 with 25% ammonia solution and heated thereby to approximately 70° C. (weight: 4350–4550 g, composition: 32–34% MHA, 29–30.5% ammonium sulfate, remainder water) were charged continuously into a first film evaporator 2 and concentrated by flash vaporization at 90° C./80 mbar during which approximately 80–90% of the total water present was expelled and trapped via condenser 3 in receiver 4. The concentrates still containing residual water were alternatingly taken up in receivers 5a, 5b loaded with MIBK in a weight ratio of 1:2 under agitation and cooling. The resulting suspension fractions were fed continuously to a second film evaporator (Sambay) 5 and azeotropically dewatered at 70°–75° C. in a vacuum. The gel-like product mixture running off was thoroughly agitated in cooled receiver 6 in MIBK under constant supplementation of the evaporation losses. The resulting suspension was discharged in portions with the aid of a suitable transport member and placed on skimmer centrifuge 9. The crystal fractions centrifuged off and washed with MIBK were collected in a storage drum for later drying. The filtrates united in filtrate container 10 were continuously fed into falling-film evaporator 11 and distilled free of solvent in a vacuum. The bottom product running off was alternatingly taken up in receivers 12a, 12b and diluted with water to a concentration of about 88%. The conditioned fractions were brought together in a storage container and balanced. The yields of MHA and ammonium sulfate were about 99% with a dimer content of the MHA of below 10%. The MHA solution had a pale yellow color, good flowability and thermal stability. The MIBK separated during the azeotropic dewatering in phase separation vessel 8 was united with the main current recovered via vapor condensation 13, 14 and returned into a new workup cycle but now as MIBK saturated with water (~2% $H_2O$).

The aqueous phases accumulated in phase separation vessel 8 were distilled in strip column 15 under a vacuum to remove residual MIBK. The MIBK again distilling over azeotropically was returned into condensation system 7 and 8 of film evaporator 5 communicating with column 15.

Figure 2:
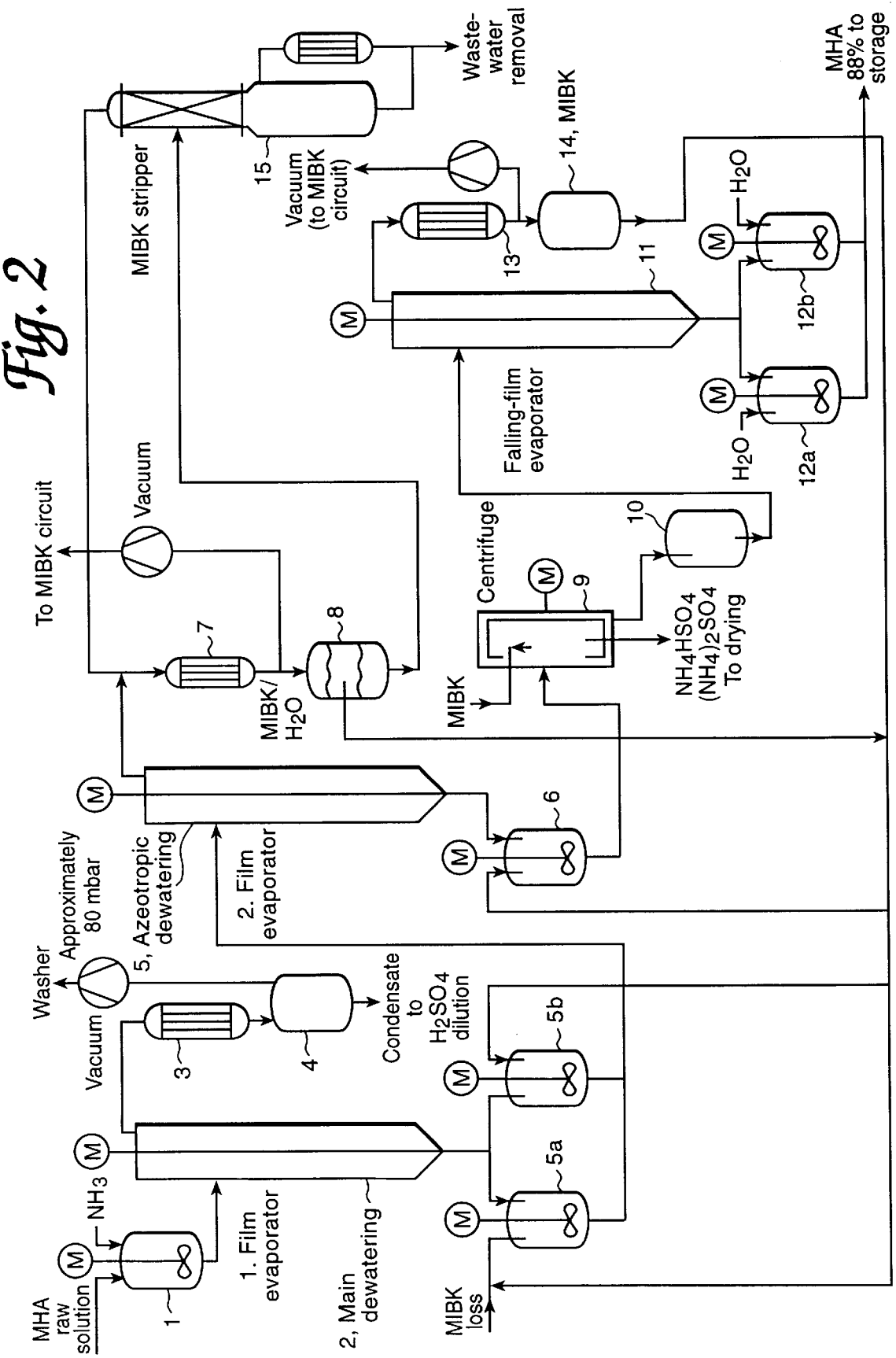
FIG. 2 shows a schematic survey for a second industrial variant of the process of the invention for producing MHA.
Figure 3:
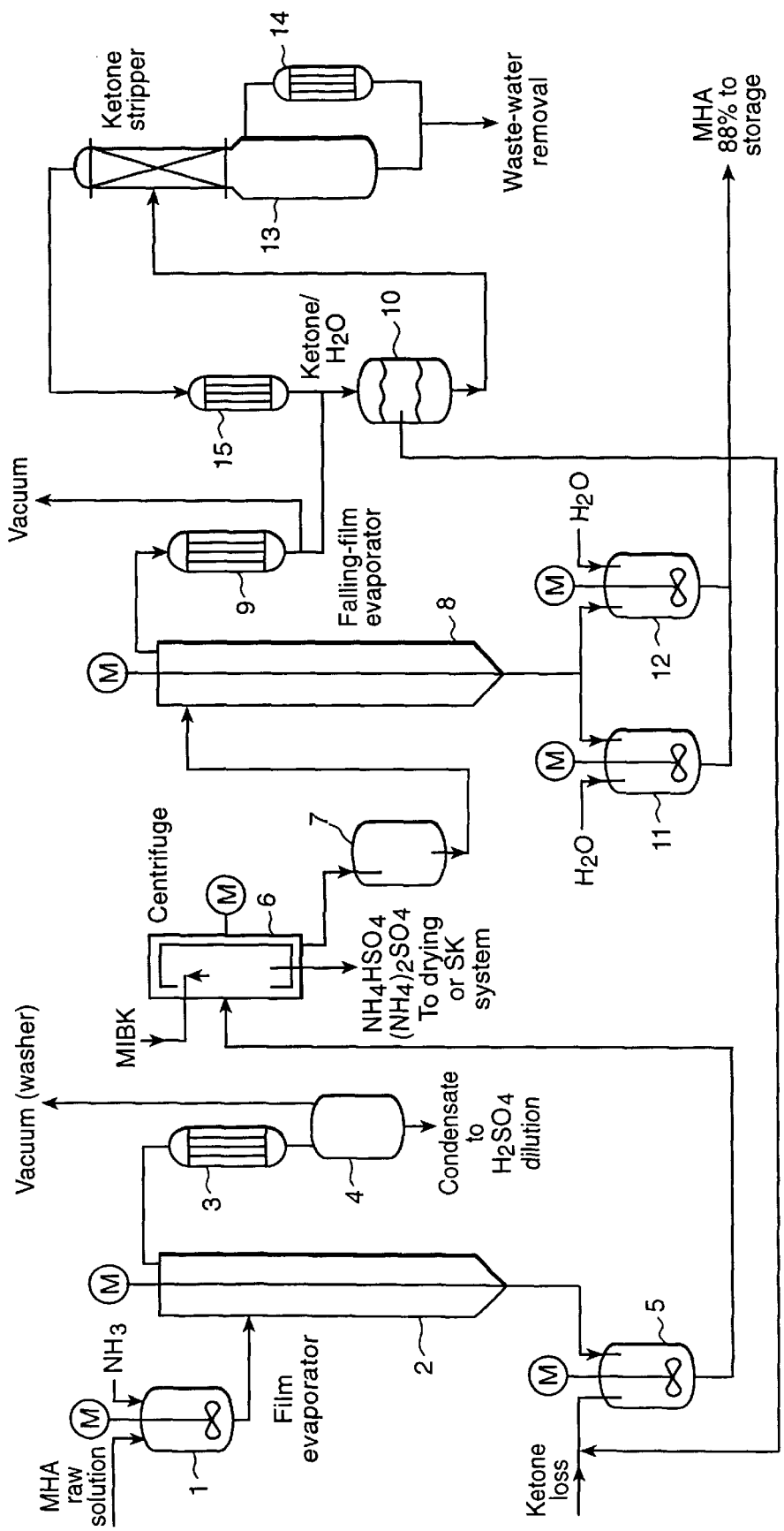
FIG. 3 shows a schematic survey for a third industrial variant of the process of the invention for producing MHA.
Figure 4:
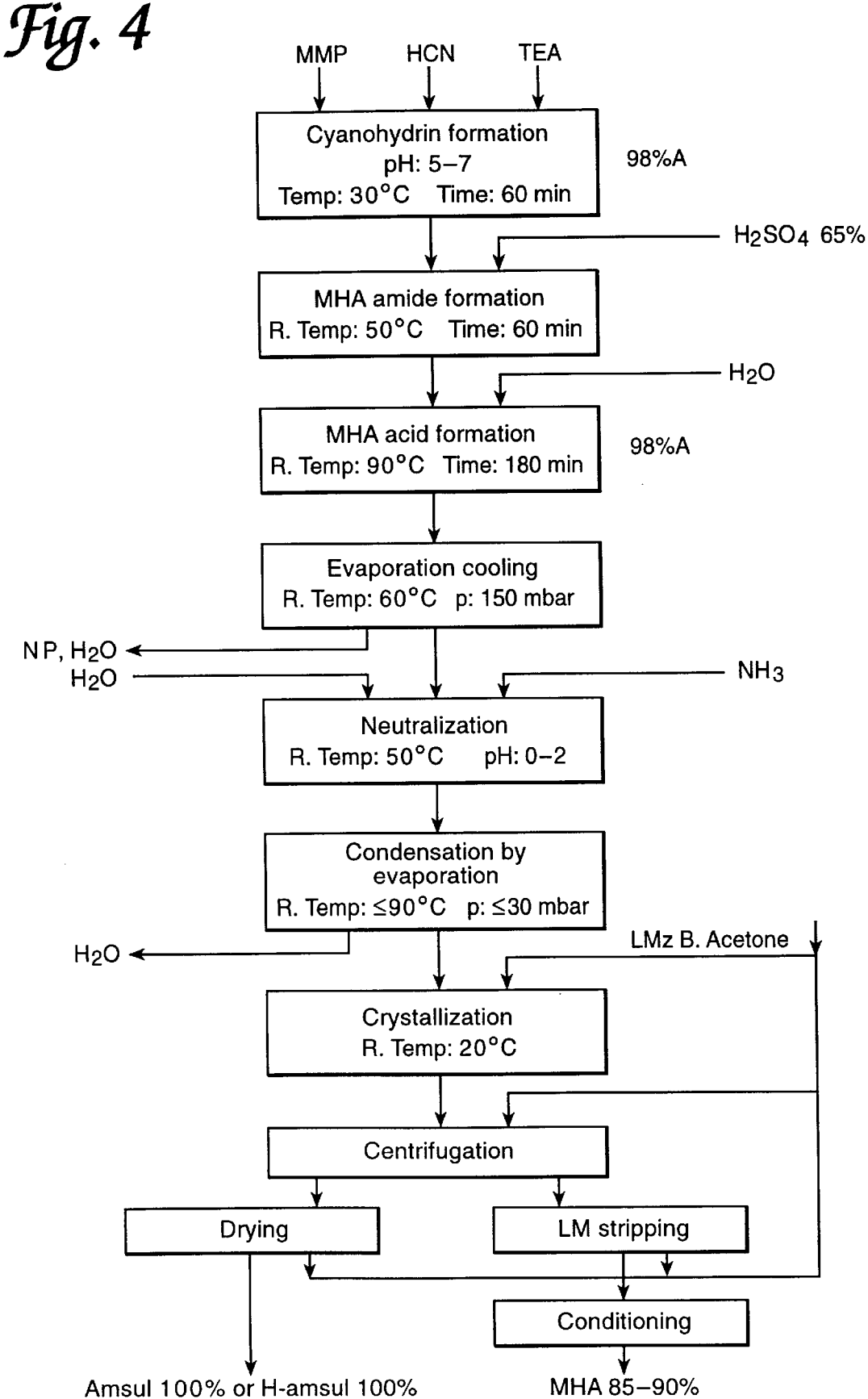
FIG. 4 shows a block diagram with the process steps of a preferred process variant of the invention.

FIG. 3 shows a simplified industrial performance of the process of the invention with any desired solvent. The significance of the reference numerals used corresponds to the reference numerals used in FIGS. 1 and 2.

Example 19

The procedure of example 18 was followed; however, the following solvents were used in succession for product separation: 1st, methylisopropylketone, 2nd, ethyl-n-amylketone, 3d, acetic acid isobutylazetate. Yields and product properties do not differ significantly from the preceding example.

Example 20

The procedure of example 18 was followed; however, methyl-t-butylether was used to separate the salt/MHA mixture and the solvent distillations in evaporation stages 5, 11, 15 of FIG. 2 were carried out under normal pressure. The results were comparable to those of example 18.

Example 21

150 l demineralized water were placed in an enamelled, double-jacketed agitator reactor with reflux condenser and waste-gas washer with connected vacuum pump and 300 kg 98% sulfuric acid (3.0 Kmoles) mixed in. 408 kg 96.5% MMP-CH were then added under intensive mixing in such a manner that after the reaction temperature of 50°–55° C. had been reached the reaction heat was able to be removed via the double jacket loaded with refrigerating brine. After the infeed was over the mixture was allowed to react 30 minutes longer and controlled for the complete conversion of the cyanohydrin. The intermediate hydrolysis product mixture consisting essentially of the acid amide MHA amide was diluted with 360 l demineralized water, heated to 90° C. and agitated 3 h at this temperature. The hydrolysis was complete thereafter and MHA amide could no longer be demonstrated. After the cooling had been removed a vacuum was applied and the temperature lowered in the course of approximately 30 minutes by evaporation cooling to approximately 65° C. while at the same time slight amounts of volatile organic matter along with proportionate amounts of water, together approximately 36 kg, were stripped off and absorbed in the waste-gas washer.

The absorption liquid was detoxified with hydrogen peroxide at pH 9 as well as deodorized and subsequently transferred to the waste-water net. After dealcoholization 1172 kg (960 l) hydrolysis solution were obtained with the composition of 37.9% MHA (with oligomers), 29.4% ammonium bisulfate and 32.5% water. The solution was pumped into a measuring receiver tempered to 65° C. and continuously drawn out of the latter by suction into a vapor-heated film evaporator which was provided with a fixed-blade rotor, had a heating area of 1.0 m$^2$ and was connected via a vapor condenser together with a receiver to a vacuum system. The solution was dewatered with the greatest possible throughput rate at 90° C./80 mbar until less than 0.5% water in the bottom product. The concentrate running off was pumped under stress relief by a lobe pump into an agitator receiver half-filled and cooled with acetone, during which the salt separated in crystalline form. After appropriate solid enrichment the suspension formed was put in portions on a link-suspended centrifuge while at the same time the discharged amount of acetone was re-supplemented in the level-regulated agitator receiver. The filtrate running from the centrifuge into a collecting tank was fed continuously into a falling-film evaporator heated by warm water and with 0.5 m$^2$ heating area which had available the same supplementary units as the film evaporator and distilled out free of solvent at 80° C./160 mbar. The concentrate running off was pumped off under stress relief with a lobe pump into a cooled agitator receiver in which the amount of water for adjusting a final concentration of 88% MHA, calculated for the entire batch, had already been placed. After the last loading and centrifugation of a centrifuge filling the filter cake was repeatedly washed out with acetone, centrifuged and collected in storage drums for subsequent drying. The acetone with less than 0.2% water recovered in the brine-cooled condensers of the distillation as well as of the salt drying carried out in a blade drier was able to re reused without rectification after replacement of loss.

After the end of the workup cycle 442 kg (98.1%) total MHA with 13.8% dimers, 2.6% trimers and 0.2% sulfate were obtained as brownish-yellow solution. In addition, 342 kg (99%) ammonium bisulfate were isolated. Approximately 285–290 kg sulfuric acid (100%) can be recovered therefrom by thermal splitting in a sulfuric acid contact system.

The procedure described in a semi-technical manner in example 21 stands as an example for a large-scale process with batchwise production and continuous workup with any desired solvent (preferably ketone) in which the resulting ammonium bisulfate is utilized without previous neutralization in a connected sulfuric acid contact system for the recovery of sulfuric acid and the formation of nitrogen.

We claim:

1. A process for producing 2-hydroxy-4-methylthiobutyric acid (MHA) in which the MHA is isolated from a reaction mixture obtained by the attachment of hydrogen cyanide (HCN) to methylmercaptopropionaldehyde (MMP) and by hydrolysis of the methylmercaptopropionaldehyde cyanohydrin (MMP-CH) obtained thereby with sulfuric acid which comprises (a) concentrating the reaction mixture by evaporation under conditions to obtain an MHA-containing salt residue substantially free of residual water,(b) subsequently treating the MHA-containing salt residue with an organic solvent under conditions to form a suspension, (c) separating solid components from the suspension under conditions to obtain an MHA-containing solution, (d) removing the organic solvent from the MHA-containing solution and recovering an MHA residue and, wherein the MHA residue is conditioned thereafter, if necessary, by the addition of water.

2. The process according to claim 1 wherein the reaction mixture is concentrated by evaporation to a residual water content of ≤5% relative to MHA+oligomers.

3. The process according to claim 1 wherein the reaction mixture is freed of residual water.

4. The process according to claim 1 wherein evaporation of the reaction mixture is carried out continuously.

5. The process according to claim 1 wherein the reaction mixture is subjected before and/or during the concentration by evaporation to an adiabatic evaporation cooling under a vacuum at approximately 60° C. or less in order to remove any volatile or odor-intensive components in the reaction mixture.

6. The process according to claim 1 wherein evaporation of the reaction mixture takes place after a previous neutralization with ammonia.

7. The process according to claim 1 wherein the MHA-containing salt residue is obtained as bottom product from (a) and is treated with acetone, methylisopropylketone, methylisobutylketone, isopropanol, toluene or tetrahydrofurane as organic solvent in (b).

8. The process according to claim 1 wherein the suspension formed in (b) is filtered, during which crystalline ammonium sulfate salts in a purity ≥99% accumulate as solid components and the MHA-containing solution accumulates.

9. The process according to claim 1 wherein the solvent is separated out of the MHA-containing solution under rectifying and/or azeotrope-forming conditions and the solvent recovered contains less than 5% water.

10. The process according to claim 1 wherein the hydrolysis of the MMP-CH is carried out in two stages and MHA amide is obtained in a first stage and MHA in a second stage.

11. The process according to claim 10 wherein MMP-CH is hydrolyzed in the first stage with 60–85% sulfuric acid in a molar ratio of 1:0.5 to 1:1.0 at temperatures between 20° and 60° C.

12. The process according to claim 11 wherein the mixture obtained in the first hydrolysis stage is free of non-reacted cyanohydrin.

13. The process according to claim 10 wherein the MHA amide is hydrolyzed in the second stage with the addition of water and further sulfuric acid up to the stoichiometric upper limit at temperatures of 90°–110° C. or under reflux conditions.

14. A process for producing 2-hydroxy-4-methylthiobutyric acid (MHA) in which the MHA is isolated from a reaction mixture obtained by the attachment of hydrogen cyanide (HCN) to methylmercaptopropionaldehyde (MMP) and by hydrolysis of methylmercaptopropionaldehyde cyanohydrin (MMP-CH) obtained thereby with sulfuric acid wherein the MHA isolated from the reaction mixture comprises a solid/liquid separation in which an essentially gelatinous or solid MHA-containing salt residue is treated with an organic solvent.

15. The process according to claim 8 wherein the ammonium sulfate salts obtained in solid form are conducted, optionally after previous evaporation of solvent remnants and being slurried with water, to a sulfuric acid—contact system for recovery of sulfuric acid.

16. The process according to claim 1 or claim 8 wherein the evaporation of the reaction mixture is carried out without previous or subsequent neutralization with ammonia, and ammonium bisulfate salts are obtained in solid form and conducted, optionally after previous evaporation of solvent remnants and slurried with water, to a sulfuric acid—contact system for recovery of sulfuric acid.

* * * * *